United States Patent [19]
Amigo et al.

[11] Patent Number: 6,056,860
[45] Date of Patent: *May 2, 2000

[54] SURFACE MODIFIED ELECTROPHORETIC CHAMBERS

[75] Inventors: M. Goretty Alonso Amigo; Randy M. McCormick, both of Santa Clara, Calif.

[73] Assignee: ACLARA Biosciences, Inc., Mountain View, Calif.

[ * ] Notice: This patent is subject to a terminal disclaimer.

[21] Appl. No.: 08/933,162

[22] Filed: Sep. 18, 1997

Related U.S. Application Data

[63] Continuation-in-part of application No. 08/715,338, Sep. 18, 1996, Pat. No. 5,935,401.

[51] Int. Cl.$^7$ .......................... G01N 27/26; G01N 27/447
[52] U.S. Cl. .......................... 204/454; 204/450; 204/451; 204/600; 204/601
[58] Field of Search .................................... 204/454, 600, 204/601, 602, 603, 604, 605, 450, 451, 452; 427/393.5

[56] References Cited

U.S. PATENT DOCUMENTS

| | | | |
|---|---|---|---|
| 2,829,066 | 4/1958 | Murdock et al. | 427/393.5 X |
| 3,429,845 | 2/1969 | Bechtold et al. | 427/393.5 X |

(List continued on next page.)

FOREIGN PATENT DOCUMENTS

| | | |
|---|---|---|
| 0 452 055 B1 | 4/1991 | European Pat. Off. . |
| 0484278 B1 | 10/1991 | European Pat. Off. . |
| 0488947 B1 | 11/1991 | European Pat. Off. . |
| 637 996 B1 | 4/1993 | European Pat. Off. . |
| 637 997 B1 | 4/1993 | European Pat. Off. . |

(List continued on next page.)

OTHER PUBLICATIONS

Schutzner et al., "Electrophoresis in Synthetic Organic Polymer Capillaries: Variation of Electroosmotic Velocity and Potential with pH and Solvent Composition," *Anal. Chem*, (1992), vol. 64, No. 17.

Nielen, "Capillary Zone Electrophoresis Using a Hollow Polypropylene Fiber," *J. High Res. Chrom.*, (1993), vol. 16, pp. 62–64.

Liu et al., "Polymeric Hollow Fibers for Capillary Electrophoresis," *J. Microcol.*, (1993), vol. 5, No. 3, pp. 243–253.

Hjerten, "High–Performance Electrophoresis Elimination of Electroendosmosis and Solute Adsorption," *J. Chrom.*, (1995), 347, pp. 191–198.

(List continued on next page.)

*Primary Examiner*—Jill Warden
*Assistant Examiner*—John S. Starsiak, Jr.
*Attorney, Agent, or Firm*—Bertram I. Rowland; Rae-Venter Law Group P.C.

[57] ABSTRACT

Electrophoretic chambers having at least a region of surface modification, and methods for their fabrication, are provided. In some embodiments the subject chambers include in the region of surface modification an anchoring polymeric layer interpenetrating the surface of the chamber and an electrophoretic polymeric layer copolymerized with the anchoring polymeric layer. The subject chambers are prepared by sequentially contacting the chamber surface with a first monomer capable of interpenetrating the surface and a second monomer capable of copolymerization with the first monomer, followed by copolymerization of the first and second monomers. In other embodiments an electrophoretic polymeric layer is noncovalently bound on the surface of a rigid polymereic base material without the aid of a separate anchoring polymeric layer. The subject devices find use in any of a variety of electrophoretic applications in which entities are moved through a medium under the influence of an applied electric field.

8 Claims, 2 Drawing Sheets

U.S. PATENT DOCUMENTS

| | | | |
|---|---|---|---|
| 4,675,300 | 6/1987 | Zare et al. | 204/452 |
| 4,680,201 | 7/1987 | Hjerten | 427/230 X |
| 4,722,777 | 2/1988 | Ogawa et al. | 204/606 |
| 4,908,112 | 3/1990 | Pace | 204/601 X |
| 4,931,328 | 6/1990 | Swedberg | 428/36.91 X |
| 4,936,974 | 6/1990 | Rose et al. | 204/603 |
| 5,006,313 | 4/1991 | Swedberg | 422/70 X |
| 5,011,586 | 4/1991 | Finney et al. | 204/466 |
| 5,039,549 | 8/1991 | Nguyen et al. | 427/54.1 |
| 5,085,756 | 2/1992 | Swedberg | 204/605 |
| 5,098,539 | 3/1992 | Shieh | 204/453 |
| 5,110,745 | 5/1992 | Kricka et al. | 436/87 |
| 5,114,768 | 5/1992 | Swedberg | 428/36.91 |
| 5,165,898 | 11/1992 | Chu et al. | 204/607 |
| 5,176,203 | 1/1993 | Larzul | 165/61 |
| 5,250,263 | 10/1993 | Manz | 422/81 |
| 5,286,356 | 2/1994 | Jones et al. | 204/452 |
| 5,296,114 | 3/1994 | Manz | 204/451 |
| 5,296,375 | 3/1994 | Kricka et al. | 435/288.5 X |
| 5,304,487 | 4/1994 | Wilding et al. | 435/29 |
| 5,332,679 | 7/1994 | Simons et al. | 436/518 |
| 5,346,672 | 9/1994 | Stapleton et al. | 422/102 |
| 5,376,252 | 12/1994 | Ekström et al. | 204/603 |
| 5,384,261 | 1/1995 | Winkler et al. | 436/518 |
| 5,427,946 | 6/1995 | Kricka et al. | 435/288.5 |
| 5,443,890 | 8/1995 | Öhman | 428/167 |
| 5,480,614 | 1/1996 | Kamahori | 422/70 |
| 5,486,335 | 1/1996 | Wilding et al. | 422/55 |
| 5,498,392 | 3/1996 | Wilding et al. | 422/68.1 |
| 5,500,071 | 3/1996 | Kaltenbach et al. | 156/272.8 |
| 5,521,319 | 5/1996 | Huber et al. | 548/364.1 |
| 5,549,796 | 8/1996 | Chu et al. | 204/457 |
| 5,571,410 | 11/1996 | Swedberg et al. | 210/198.2 |
| 5,580,435 | 12/1996 | Kovacs | 204/603 |
| 5,585,069 | 12/1996 | Zanzucchi et al. | 422/100 |
| 5,587,128 | 12/1996 | Wilding et al. | 422/50 |
| 5,593,838 | 1/1997 | Zanzucchi et al. | 435/6 |
| 5,603,351 | 2/1997 | Cherukuri et al. | 137/597 |
| 5,630,924 | 5/1997 | Fuchs et al. | 204/601 |
| 5,632,876 | 5/1997 | Zanzucchi et al. | 204/600 |
| 5,635,358 | 6/1997 | Wilding et al. | 435/7.2 |
| 5,637,469 | 6/1997 | Wilding et al. | 435/7.21 |
| 5,639,423 | 6/1997 | Northrup et al. | 422/50 |
| 5,641,400 | 6/1997 | Kaltenbach et al. | 210/198.2 |
| 5,643,738 | 7/1997 | Zanzucchi et al. | 435/6 |
| 5,645,702 | 7/1997 | Witt et al. | 204/601 |
| 5,646,039 | 7/1997 | Northrup et al. | 435/287.2 |
| 5,646,048 | 7/1997 | Templin et al. | 436/180 |
| 5,658,413 | 8/1997 | Kaltenbach et al. | 156/272.8 |
| 5,674,742 | 10/1997 | Northrup et al. | 435/286.5 |
| 5,681,484 | 10/1997 | Zanzucchi et al. | 216/2 |
| 5,726,026 | 3/1998 | Wilding et al. | 435/7.21 |
| 5,744,366 | 4/1998 | Kricka et al. | 436/63 |
| 5,747,169 | 5/1998 | Fan et al. | 428/426 |
| 5,755,942 | 5/1998 | Zanzucchi et al. | 204/454 |

FOREIGN PATENT DOCUMENTS

| | | |
|---|---|---|
| 637 998 B1 | 4/1993 | European Pat. Off. . |
| 0 665 430 A1 | 1/1994 | European Pat. Off. . |
| 0527905 B1 | 11/1995 | European Pat. Off. . |
| WO90/04645 | 5/1990 | WIPO . |
| WO91/13338 | 9/1991 | WIPO . |
| WO91/15750 | 10/1991 | WIPO . |
| WO93/20449 | 10/1993 | WIPO . |
| WO94/12871 | 6/1994 | WIPO . |
| WO96/15450 | 5/1996 | WIPO . |
| WO96/15576 | 5/1996 | WIPO . |
| WO96/39252 | 12/1996 | WIPO . |
| WO96/39260 | 12/1996 | WIPO . |
| WO96/42004 | 12/1996 | WIPO . |
| WO97/01755 | 1/1997 | WIPO . |
| WO97/16561 | 5/1997 | WIPO . |
| WO97/16835 | 5/1997 | WIPO . |
| WO97/17324 | 7/1997 | WIPO . |
| WO97/37755 | 10/1997 | WIPO . |
| WO97/43629 | 11/1997 | WIPO . |
| WO98/00705 | 1/1998 | WIPO . |
| WO98/13683 | 4/1998 | WIPO . |

OTHER PUBLICATIONS

"Adhesion and Bonding" In: *Enclycopedia of Polymer Science and Engineering, Wiley Interscience*, (1995) vol. 1, vol. 1, pp. 476–517.

Finn et al., "Synthesis of Biotinyl Derivatives of Peptide Hormones and Other Biological Materials," (1985) No month available, Methods in Enzymology, vol. 109, pp. 418–445.

Lichstein et al., "Combinability Of Avidin And Streptavidin With Analogs Of Biotin," (May 17, 1965) Biochemical and Biophysical Research Communications, vol. 20, No. 1, pp. 41–45.

Green, "Avidin and Streptavidin," (1990) No month available, Methods in Enzymology, vol. 184, pp. 51–67.

Finn et al., "Ligands for Insulin Receptor Isolation," (1984) No month available, Biochemistry, pp. 2554–2558.

Tong et al., "Solid–Phase Method for the Purification of DNA Sequencing Reactions," (Nov. 15, 1992) Analytical Chemistry, vol. 64, No. 22, pp. 2672–2677.

SURFACE MODIFIED ELECTROPHORETIC CHAMBERS

CROSS-REFERENCE TO RELATED APPLICATION

This application is a continuation-in-part of U.S. patent application Ser. No. 08/715,338, filed Sep. 18, 1996 now U.S. Pat. No. 5,935,401.

BACKGROUND

This invention relates to electrophoresis.

Electrophoresis, in which entities are moved through a medium as a result of an applied electric field, has become an increasingly indispensable tool in biotechnology and related fields. In electrophoresis, the electrophoretic medium through which the entities are moved is housed in an electrophoretic chamber. A variety of different chamber configurations find use, including slab gel holders, columns or tubes, microbore capillaries, grooves or channels on a substrate surface etc., where advantages and disadvantages are associated with each particular configuration.

The particular material from which an electrophoretic chamber is fabricated can have a significant impact on the results of the application in which the chamber is employed. Some materials, e.g., fused silica, have charged surfaces under conditions of electrophoresis which give rise to electroosmotic flow. The presence of electroosmotic flow (EOF) can change the movement profile of the entities through the medium during electrophoresis. Certain materials can also adsorb entities from the medium, such as proteins and other biomolecules, which can adversely affect the results of a particular application.

As knowledge of the effect of surface properties on the movement of entities through a medium in electrophoretic applications grows, there is an increasing interest in the development of methods to tailor the surface properties of the electrophoretic chamber to meet the needs of a particular application. For example, it may be desirable to have a surface modified to reduce or enhance EOF through the chamber, to reduce or enhance analyte adsorption to the walls of the chamber, to provide for stable attachment of a gel network to the surface of the chamber, and the like.

Although fused silica has traditionally been the material of choice from which electrophoretic chambers are fabricated, of increasing interest as an alternative material are plastics. Various means have been developed for the surface modification of materials employed in electrophoretic applications. Surface modification techniques that have been employed include techniques based on the physical or chemical alteration of the material surface, e.g., etching, chemical modification, and coating a new material over the existing surface, e.g., solvent coating or thin film deposition by chemical or vapor deposition, radiation grafting, chemical grafting and RF-plasma. The particular surface modification means employed necessarily depends on the material to be modified. For methods specifically directed to the treatment of plastic surfaces of electrophoretic chambers, see EP 665 430 A1 and EP 452 055 B1.

Despite the availability of a number of different plastic surface modification techniques, there is a continued interest in the development of new surface modification procedures which would increase the number of different available methods and provide for further surface property tailoring opportunities to best meet the needs of a particular application.

U.S. Pat. No. 4,680,201 describes a method for covalently attaching a polyacrylamide surface layer to the inner surface of fused silica capillaries. U.S. Pat. No. 5,433,898 describes a process for preparing material for use in the construction of contact lenses comprising two or more polymers.

EP 665 430 A1 and EP 452 055 B1 describe use of surface modified polymeric capillaries in electrophoresis.

Additional references describing electrophoresis in various surface modified capillaries include: Gilges et al., "Capillary Zone Electrophoresis Separations of Basic and Acidic Proteins Using Poly(vinyl alcohol) Coatings in Fused Silica Capillaries," Anal. Chem. (1994) 66:2038–2046; Rohlicek et al., "Determination of the Isoelectric Point of the Capillary Wall in Capillary Electrophoresis, Application to Plastic Capillaries," J. Chrom. A. (1994) 662:369–373; Schütziner & Kenndler, "Electrophoresis in Synthetic Organic Polymer Capillaries: Variation of Electroosmotic Velocity and $\zeta$ Potential with pH and Solvent Composition," Anal. Chem. (1992) 64: 1991–1995; Nielen, "Capillary Zone Electrophoresis Using a Hollow Polypropylene Fiber," J. High Resolution Chrom. (1993) 16:62–64; and Liu et al., "Polymeric Hollow Fibers for Capillary Electrophoresis," J. Microcol. Sep. (1993) 5:245–253; Hjertén, "High Performance Electrophoresis Elimination of Electroendosmosis and Solute Adsorption," J. Chromatogr. (1985) 347:191–198.

Encyclopedia of Polymer Science and Engineering, "Adhesion and Bonding," Vol. 1, pp. 476 et seq. (Wiley Interscience, 1985) describes reactive adhesives based on the surface interpenetration of reactive monomers.

A review of surface modification of polymer materials is provided in Ratner, Biosensors & Bioelectronics (1995) 10:797–804.

SUMMARY OF THE INVENTION

Electrophoretic chambers having at least a region of surface modification, as well as methods for their fabrication, are provided. The subject devices find use in a wide variety of electrophoretic applications in which entities are moved through a medium in response to an applied electric field.

In one aspect of the invention the region of surface modification includes an electrophoretic polymeric layer, which provides for the tailored surface properties in the modified region, stably bound to the polymeric material of the chamber through copolymerization with an anchoring polymeric layer that interpenetrates the surface of the chamber. The subject chambers are prepared by contacting the surface of the chamber with a first monomer capable of interpenetrating the surface. The resultant interpenetrated surface is then contacted with a second monomer, followed by copolymerization of the first and second monomers.

In another aspect of the invention, the region of surface modification includes a polymeric layer which is bound to the interior surface of the polymeric material of the chamber wall by non-covalent molecular interactions without the aid of a second anchoring polymeric layer. The noncovalently bound polymeric layer is applied to the surface by contacting a solution containing the dissolved polymer with the interior surface of the chamber, and allowing the polymer in solution to form molecular interactions with the surface to form the surface coating. The polymeric layer may be immobilized at the surface by interpenetration of the polymeric material of the chamber wall, by ionic interactions, or by hydrophobic interactions.

DETAILED DESCRIPTION

Electrophoretic chambers having at least one region of surface modification, as well as methods for their fabrication, are provided.

In the region of surface modification, where the term region encompasses anywhere from the entire inner surface of the chambers to only a fraction thereof, the chambers comprise a rigid polymeric base material, an anchoring polymeric layer penetrating the surface of the base material and an electrophoretic polymeric layer, which provides the tailored surface properties, copolymerized with the anchoring polymeric layer.

Alternatively, in the region of surface modification the chambers comprise a rigid polymeric base material and an electrophoretic polymeric layer which is noncovalently bound on the surface material without the aid of a separate anchoring polymeric layer.

In further describing the subject invention, the chambers will first be described in greater detail followed by a discussion of the methods used to fabricate the subject chambers.

In the subject chambers, at least that portion of the chamber in the region of surface modification will be fabricated from a solid, rigid polymeric material that is insoluble in aqueous media. As the polymeric material is solid and rigid, it will have sufficient strength to serve as a mechanical support for an electrophoretic medium, such as a buffer or gel. Although only the material in the region of surface modification will necessarily be the rigid, solid polymeric base material, the entire chamber, e.g., capillary or planar substrate having a microchannel on its surface, may be fabricated from the base polymeric material. Alternatively, the chamber may be fabricated from two or more different materials, so one has a chamber fabricated from a composite material.

For example, in the walls of the chamber the base polymeric material can be present over a layer of another material, where the different material may serve to modify the physical properties of the substrate. Where desired, the second material present in the composite substrate may be a heat dissipating material which serves to absorb heat produced in the electrophoretic medium during electrophoresis. Materials that provide for heat absorption and dissipation and may be present in a composite substrate include glasses, ceramics, metals and the like. Specific heat absorbent materials of interest, depending on the nature of the microchannel, include aluminum, copper, glass and the like. Where the base polymeric material is a composite, the layer of rigid polymeric material will be sufficiently thick so that, taken by itself, it can serve as a mechanical support and containment means for the medium contained by it. The thickness of the base polymeric substrate will necessarily depend on the structural configuration of the final device comprising the compositions, e.g., whether the device is a slab gel holder, capillary, microchannel, etc., as described in greater detail below, as well as the bulk properties of the base material, such as its tensile strength, brittleness, flexural strength, and the like. Generally, the thickness of the substrate will be at least about 0.25 mm, more usually at least about 0.5 mm and will generally not exceed about 10 mm, and will usually not exceed about 5 mm.

Polymeric materials suitable for use as the base material in at least the region of surface modification will be moldable and extrudable into a rigid objects that are electrically non-conductive, have high resistivity to electric fields and are stable in the presence of a variety of electrophoretic media under electrophoretic conditions, including aqueous solutions comprising high salt concentrations and having pH ranges from 2 to 12. The polymeric material may comprise one or more different polymers, but will usually comprise no more than four different polymers, more usually no more than two different polymers. The polymers may be homo- or copolymeric, and be uncrosslinked or crosslinked. Polymers finding use will be synthetic, usually organic and may be addition or condensation polymers. Polymeric materials from which electrophoretic chambers have been fabricated and are amenable to surface modification by the subject invention include: acrylics, e.g., polymethylmethacrylate; polycarbonate; polyethylene terepthalate; polystyrene; polyethylene; polypropylene; polyvinyl chloride; polyfluorocarbon; polybutylene terepthalate; polyvinyl alcohol; polyetherether ketone; polyamides or nylons; phenyl silicones; polyurethanes; acrylonitrile-styrene copolymers, copolymers of ethylmethacrylate and methylmethacrylate, and blends of polymethylmethacrylate and polyethylmethacrylate, and the like.

Depending on the particular device, as well as the detection method and system in which it is employed, it may be desirable for the polymeric material to be optically transparent, where optically transparent means that the material allows light of wavelengths ranging from 180 to 1500 nm, usually from 220 to 800 nm, more usually from 250 to 800 nm, to have low transmission losses. Such light transmissive polymeric materials will be characterized by low crystallinity and include polycarbonate, polyethylene terepthalate, polystyrene, polymethylpentene, fluorocarbon copolymers, and the like, as well as the acrylic polymeric materials described in co-pending U.S. patent applications Ser. Nos. 08/627,484, filed Apr. 4, 1996, and 08/878,437, filed Jun. 18, 1997, the disclosures of which are hereby incorporated herein by reference, with polyacrylates, particularly polymethacrylates, and more particularly polymethylmethacrylate (PMMA) being preferred materials.

In some embodiments, in the region of surface modification, interpenetrating the internal surface of the electrophoretic chambers will be an anchoring polymeric layer. By interpenetrating is meant that the anchoring polymeric layer interdiffuses beneath the surface of the solid polymeric material. The interdiffused anchoring polymeric layer comprises linear polymeric strands, that may be either homopolymeric or copolymeric, extending throughout the region of the base material adjacent to the surface. In other words, in the interdiffused region there are linear polymeric strands intertwined throughout the base polymeric network, with substantially no grafting of the anchoring polymeric strands to the base polymeric strands. Since the method used to prepare the subject chambers requires a specific relationship between the base material and the monomer from which the anchoring polymeric layer is prepared (described in greater detail below), depending on the particular nature of the solid base polymeric material, the anchoring polymer may be polymerized from one or more of a variety of different monomers, where the monomers will generally be addition polymerizable ethylene containing monomers, usually vinylic, acrylic or pyrrolic, where the term acrylic includes methacrylic, where the acrylic monomers may be esters or amides. Specific anchoring polymers of interest are those polymerized from N-vinyl pyrrolidone, hydroxyethylmethacrylate, dimethyl acrylamide, hydroxymethylacrylamide, ethylene glycol dimethacrylate, glycerol methacrylate, glycidyl methacrylate, and the like, where polymers polymerized from dimethylacrylamide, N-vinyl pyrrolidone, hydroxymethylacrylamide and the like are preferable when the base polymeric material is polymethylmethacrylate. The distance to which the interdiffused portion of the base polymeric material extends beneath the surface of the base material will be a distance sufficient so that, when copolymerized with the surface electrophoretic layer, the interdiffused strands of the anchoring polymeric layer stably secure the surface electrophoretic layer to the base polymeric material surface. The interdiffused region of the base polymeric material will range in thickness to as much as about 1500 Å, usually at least about 15 Å; usually the interdiffused region is no thicker than about 700 Å, more usually no thicker than about 500 Å. There will be no sharp demarcation at the border defining the extent of the interdiffused anchoring polymeric layer.

The electrophoretic layer stably secured to the surface of the base material in the region of surface modification can serve to impart a number of different properties to the surface, including changing the inherent surface charge of the chamber, providing for reactive functional groups, providing for an electrophoretic medium that substantially fills the inner volume of the chamber, and the like. Although the electrophoretic layer may be polymerized from a variety of different monomeric compounds depending on the purpose of the layer, it will be polymerized from addition polymerizable monomers capable of copolymerization with the interpenetrated monomers of the anchoring layer.

By changing the surface charge characteristics of the base polymeric material, the electrophoretic layer can serve a variety of purposes, including enhancing or reducing the occurrence of EOF in the chamber, providing for enhancement, reduction or selectivity in entity adsorption to the surface of the chamber, etc. For example, an electrophoretic layer polymerized from appropriate monomers can be employed in order to mask or cover any surface charge inherent in the solid polymeric base material under conditions of electrophoresis. By masking the surface charge, one can substantially reduce or eliminate the occurrence of EOF during electrophoresis. Electrophoretic layers which are suitable for at least reducing if not substantially eliminating the occurrence of EOF include those hydrophilic polymers having uncharged side groups, where the side groups may be amides, esters, pyrroles, hydroxides and the like. Specific electrophoretic layers providing for reduced EOF include: polyacrylamide and polymethacrylamide, polyhydroxyethylmethacrylate, polyvinylpyrrolidone, polyhydroxymethylacrylamide and the like. One could also enhance the magnitude of the EOF, or reverse the direction of the EOF, by having an electrophoretic layer polymerized from monomers comprising charged groups of the same charge as the surface charge of the chamber. By selection of an electrophoretic layer polymerized from monomers having appropriately charged groups, one can also provide for a reversal in the direction of EOF through the chamber. Charged groups of interest that may be present in the electrophoretic polymeric layer include carboxylic, sulfonic, phosphoryl, amine, and the like, where specific electrophoretic layers finding use in the enhancement or reversal of EOF include carboxylic, sulfonic, amine, and the like.

Instead of, or in addition to, changing the EOF in the chamber during electrophoresis, the electrophoretic layer can provide for a reduction, including a substantial elimination, of the adsorption of biomolecules to the surface of the chamber. To accomplish a reduction in the adsorption of biomolecules to the chamber surface, the electrophoretic layer can be provided that comprises hydrophilic groups having no net electrical charge, where such groups include both neutral groups such as those described above, e.g., polyacrylamide, copolymers of polyethyleneglycol acrylates of molecular weight lower than 1000 dal, and polymers comprising zwitterionic groups, such as alanyl, betaine, sulfobetaine and choline derivatives, and the like. Alternatively, one could enhance the adsorption of entities to the surface of the chamber, as well as provide for the selective adsorption of a particular class of entities, through the presence of the electrophoretic layer. Specific electrophoretic layers for reducing surface adsorption include polyacrylamide while specific electrophoretic layers for enhancing surface adsorption include polyacrylamide-2-methylpropane sulfonic acid.

The electrophoretic layer may also provide for the presence of a variety of reactive functional groups on the surface of the chamber in the region of modification, such as hydroxy, amino, epoxy, carboxy, amide, isocyanate, aldehyde, sulfonic and the like. By appropriate choice of monomer or monomers, the electrophoretic layer can provide for a single type of functional group or a plurality of different functional groups in the region of the surface modification. The presence of reactive functional groups on the surface of the chamber can be useful where it is desired to covalently bond agents to the surface, e.g., enzymes, proteins, antibodies, dies, pH modifiers, complexing agents, etc. For example, for the covalent attachment of proteins comprising primary or secondary amino groups, an electrophoretic layer comprising epoxide and aldehyde groups will be of interest. Specific electrophoretic polymeric materials of interest comprising reaction functional groups include: copolymers of glycidyl methacrylate and acrolein and the like.

The electrophoretic layer can also serve as an electrophoretic medium through which entities are moved in electrophoretic applications, where the electrophoretic layer is capable of providing for electrophoretic sieving as the entities move through the medium under the influence of the applied electric field. In this embodiment of the subject invention, the electrophoretic layer will substantially fill the entire inner volume of the electrophoretic chamber, at least in the volume bound by the region of surface modification, where the layer may comprise crosslinked and/or non-crosslinked polymers. Polymeric gel media suitable for use in electrophoresis are disclosed in Barron & Blanch, Separation & Purification Methods, (1995) 24:1–118. Specific electrophoretic layers capable of serving as electrophoretic layers are those polymerized from addition polymerizable ethylene-containing monomers, usually vinylic, acrylic or pyrrolic, with polyacrylamides being preferred. Also of interest in certain applications, e.g., preparative applications, are gels comprising reactive groups, such as amino groups, sulfonic groups, and the like.

The subject electrophoretic chambers may be formed in any of a variety of different configurations. Chambers having walls capable of being modified according to the subject invention include slab gel chambers, tubes, columns, as well as microchannel chambers, such as capillaries and trenches on the surface of planar polymeric substrate. As discussed above, the entire inner surface of the chamber may be modified to comprise the electrophoretic layer, or only a region of the inner surface may be so modified. In addition, the chambers may comprise one or more regions of surface modification, where when a plurality of regions of surface modification are provided, one has the opportunity to have a plurality of different electrophoretic layers on the surface of the chamber, which increases the variety of different applications in which the chambers may be used. For example, a chamber could be prepared having a first region in which the electrophoretic layer is a gel containing an ionically charged group, e.g., carboxy, sulfonic, amino, etc., that provides for ion exchange. Downstream from the first region could be a second region comprising an enzyme that converts a sample component to a desired product. Downstream from the second region could then be a third region modified to comprise an electrophoretic sieving medium, e.g., cross linked polyacrylamide, in which the enzyme product is separated from the remaining sample components.

In some embodiments of particular interest the electrophoretic chamber is a microchannel. The microchannels may be open or closed, where by "open" is meant that the internal volume of the microchannel is not completely separated on at least one longitudinal side from the external environment, while by "closed" is meant that the internal volume of the channel is completely separated longitudinally from the external environment. Examples of open microchannels include troughs, trenches and the like, present on the surface of a planar substrate. Closed channels are exemplified by cylinders, tubes, capillaries and the like; and by troughs, trenches and the like formed on the surface of a planar substrate and enclosed by a suitable cover The subject microchannels will have micro scale cross-sectional inner dimensions, such that the inner cross-sectional dimensions of the microchannels will be greater than 1 $\mu$m and less than 1000 $\mu$m. Generally, the cross-sectional inner dimension(s) of the microchannel, i.e. width, depth or diameter depending on the particular nature of the channel, will generally range from about 1 to 200 $\mu$m, usually from about 10 to 150 $\mu$m, more usually from about 20 to 100 $\mu$m, with the total inner cross sectional area of the microchannel providing for capillary flow through the channel, and ranging from about 100 to 40000 $\mu m^2$, usually from about 400 to 25,000 $\mu m^2$. The inner cross-sectional shape of the microchannel may vary among a number of different configurations, including rectangular, square, rhombic, triangular or V-shaped, circular, semicircular, ellipsoid and the like. The length of the microchannel will necessarily depend on the specific nature of the vessel as well as the electrophoretic device in which it is to be employed. For example, where the microchannel is a trough or trench in a substrate, the length of the microchannel may range from about 0.1 to 100 cm, and will generally range from about 1 to 20 cm, usually from about 1 to 10 cm, and more usually from about 5 to 10 cm, while for capillaries the length will generally range from about 10 to 100 cm, usually from about 10 to 75 cm, more usually from about 20 to 50 cm. Where the subject microvessel is contained within a capillary, the thickness of the wall of the capillary may range from about 50 to 1000 $\mu$m, usually from about 100 to 500 $\mu$m, more usually from about 100 to 150 $\mu$m, to provide a capillary with an outer diameter ranging from about 100 to 2000 $\mu$m, usually from about 150 to 400 $\mu$m.

Where the microchannel is a trench or trough extending downward from the surface of a substrate, conveniently a groove in the substrate, the substrate may be square, rectangular, circular and the like, and will have dimensions which will vary considerably depending on the intended use of the microchannel. Where the substrate has card-like or substantially regular parallelepiped dimensions, the length of the substrate will typically range from about 2 to 200 mm, the width of the substrate will typically range from about 2 to 200 mm, while the thickness of the substrate will typically range from about 0.1 to 10 mm. One or more, usually at least 2 and up to 100 or more, microchannels may be present on or at the surface of the substrate, where when a plurality of microchannels are present at the substrate surface, the possibility exists to have a number of different electrophoretic applications running at the same time on a single substrate. The microchannel(s) present in the substrate surface can be linear, branched or in some other convenient configuration. With branched microchannels or trenches, the possibility exists to have a first trench or channel intersected by one or more side channels, where the side channels may intersect the main channel at any convenient angle. In branched configurations, the chamber will comprise a main microchannel in intersecting relationship with at least one secondary microchannel, where at least one pair of electrodes will be associated with each microchannel, with one member of the pair being positioned at either of the termini of the channel, in order to apply an electric field to the medium in the microchannel. See, e.g., U.S. Pat. No. 5,126,022, and U.S. patent applications Ser. Nos. [08/###,###], filed Jul. 30, 1997 [A-62855-1/RFT/BK], the disclosure of which is hereby incorporated herein by reference.

As the microchannel(s) present on the substrate surface may be open, it may be desirable to separate the internal volume of the channel, and thereby the medium housed in the channel, from the external environment. In such instances a cover plate can be employed which rests on the surface of the substrate and thereby separates the internal volume of the channel from the environment. The cover plate may be fabricated from any of a number of different materials, including fused silica, acrylic polymeric materials, and the like. Where necessary and desirable, one or more of the cover plate surfaces may be treated to control (that is, to reduce or augment or the change the direction of) any EOF that may arise during electrophoresis. A number of different methods are known which reduce or eliminate EOF. Alternatively, where the cover plate is a rigid polymeric material, the method of the subject invention can be employed to appropriately modify the surface. As with the substrate, the coverplate may be fabricated from a single type of material or be a composite of one or more, usually two, materials. See, e.g., U.S. patent application Ser. No. 08/878,437, filed Jun. 18, 1997, the disclosure of which is hereby incorporated herein by reference.

Usually, either the cover plate or the substrate will be provided with one or more apertures or wells for introduction of sample or solvents or buffers and the like into the microchannel structure. The walls of such apertures or wells can if desired be treated according to the invention to alter the mobility of fluids or entities in the fluids into or out from the aperture or well, or to anchor particular reagents on the walls of such structures.

The thickness of the cover plate will usually range from about 0.01 to 10 mm, more usually from about 0.1 to 1.0 mm, where the length and width of the cover plate may be similar to, or different from, the length and width of the substrate, but will usually be substantially the same as those of the substrate. The cover plate may have substantially smooth, planar, flat surfaces, or optionally may be a mirror image of the substrate. Although not necessary, the cover plate will generally be sealed to the substrate. The cover plate and substrate may be sealed using any convenient means, such as ultrasonic welding, pressure, thermoprocessing, adhesives, sealants, physical conformance and the like. See, e.g., U.S. patent application Ser. No. 08/878,437, supra.

The electrophoretic chambers can be used in any of a variety of electrophoretic devices. Numerous electrophoretic devices are known in the art, and include devices which require manual operation as well as automated devices requiring a minimal amount of operator interaction. The electrophoretic chambers of any of these devices can be substituted with the subject electrophoretic chambers of analogous configuration.

In preparing the subject electrophoretic chambers, the base polymeric layer is contacted sequentially with first and second monomer compositions which are then subsequently copolymerized to produce the region of surface modification. Copolymerization with the first and second monomers will be through addition polymerization, with the first and second monomers containing polymerizable ethylene groups, usually vinylic monomers, where at least the second monomer will be different from the monomer(s) from which the base polymeric material is polymerized, where the first and second monomers may be the same or different and are usually different, so that at least the electrophoretic layer differs from the rigid polymeric base material. In those select situations where the first and second monomers are the same, the two step process of the subject invention allows in the first step for deep interpenetration of the monomer in a solvent selected to promote interpenetration by effective swelling of the polymer substrate. In the second step a second solvent, suitable for polymerization, carries the monomer and other polymerization components to form the electrophoretic layer effectively anchored to the solid polymeric substrate surface. As the first and second monomers are copolymerized and are usually different, the kinetic copolymerization relationship between the first and second monomers will lie between ideal and alternating, i.e. $0<r_1r_2<1$, where the relationship will be closer to ideal, with $r_1r_2$ usually being from 0 to 2, more usually between 0 and 1.

The first step is to contact the region to be modified with a first monomer capable of interpenetrating the surface. In interpenetrating the surface of the base polymeric material, the first monomer swells the surface of the base polymeric material and incorporates or becomes embedded beneath the surface of the material, where it positions itself among the polymeric strands of the base material. The distance to which the first monomer penetrates below the surface of the base material will be at least about 15 Å, in some embodiments at least about 30 Å and may be as great as about 1500 Å or greater, but will usually not exceed about 500 Å. Although the first monomer swells the surface of the polymeric material through interpenetration, because the interdiffused region extends only to at most a few nanometers below the surface of the layer, the bulk properties of the material, such as water solubility or rigidity, will not be changed as a result of interpenetration.

Because the first monomer must be capable of penetrating the surface of the base polymeric material, the first monomer employed will be chosen in view of several different considerations, including: (a) the particular chemical structure and physical morphology of the polymeric base material; (b) the similarity in the solubility parameters between the first monomer and the base polymeric material; (c) the nature of the electrophoretic layer with which it is to be copolymerized; and the like. Usually, small molecular systems are employed, the monomers including ethylene polymerizable groups, and preferably containing O or N, where the O or N may in some embodiments be part of a cyclic structure, and where the N can be mono- or di-substituted. For acrylic polymeric base materials, e.g., polymethacrylates, first monomers that find use include addition polymerizable ethylene containing monomers, usually vinylic, acrylic or pyrrolic monomers. Substituents, when present on the N, will generally be lower alkyls, usually C4 or lower, more usually C2 or lower, particularly methyl, with acrylic and pyrrolic monomers being of interest, with specific monomers of interest being dimethylacrylamide, N-vinyl pyrrolidone, methyl methacrylate and the like.

In contacting the first monomer with the base polymeric material, the first monomer may be present as a pure liquid or in a solvent, where the solvent preferably promotes the swelling of the surface of the base material and the interpenetration of the first monomer. Thus, the solvent will also generally have a similar solubility parameter to that of the base material. For acrylic base materials, solvents of interest include lower alkanols, such as methanol, isopropanol and the like. Where the first monomer is present in a solvent, the first monomer will typically be present in an amount ranging from about 1 to 100% by volume, usually from about 3 to 75% by volume, and more usually from about 3 to 50% by volume. Contact may be accomplished under dynamic or static conditions, as is convenient. Under dynamic conditions, the first monomer or solution thereof will be moved through the chamber at a flow rate that ranges from about 10 µl/min to 5 ml/min, more usually from about 25 µl/min to 3 ml/min.

The parameters of the contacting step will be selected to achieve the desired level of surface swelling and interpenetration of the first monomer without comprising the bulk mechanical properties of the base polymeric material. Parameters that will be chosen accordingly include duration of contact, nature of solvent, concentration of monomer in solvent, temperature and the like. Contact will generally be maintained for a period of time ranging from about 0.25 to 4 hr, usually from about 0.5 to 2 hr, and more usually from about 0.5 to 1 hr. After sufficient time has elapsed for the first monomer to interpenetrate the polymeric surface, excess first monomer will be removed from the surface. The excess first monomer may be removed using any convenient means, such as wiping, washing, flushing nitrogen or air under pressure and the like.

The next step in the subject method is to contact the interpenetrated or interdiffused surface of the base material with a second monomer composition. The second monomer will be copolymerizerable with the first monomer through addition polymerization, and will usually be vinylic. The vinylic second monomer will comprise a moiety which imparts the particular surface modification characteristics to the electrophoretic layer into which it is polymerized. For electrophoretic layers that modify the inherent surface charge of the base material under conditions of electrophoresis, the second monomer will be hydrophilic and can comprise neutral or charged groups, depending on the purpose of the electrophoretic layer. Where the electrophoretic layer is to reduce or eliminate the occurrence of EOF through the chamber during electrophoresis, second monomers that find use include those monomers having neutral hydrophilic groups, such as carbonyls, including acrylic and pyrrolic monomers, where acrylic monomers may be esters or amides. Specific second monomers of interest for use in the reduction of EOF include: acrylamide, hydroxyethylmethacrylate, vinyl pyrrolidone, end-capped polyethylene glycol acrylates of molecular weight lower than 1000, and zwitterionic monomers such as the betaine derivatives, and the like. For enhancing the magnitude of, or reversing the direction of, EOF through the chamber, the second monomer can be a monomer comprising a charged group, where the charged group can be negative or positive, where negatively charged groups include carboxylic groups, sulfonic groups, phosphoryl groups, and the like, as found in monomers such as vinylic acids, e.g., acrylic acid, methacrylic acid, and the like, while positively charged groups include amino, and the like, as found in 2-(dimethylamino) ethyl acrylate, 2-(diethylamino)ethyl ethacrylate and the like.

Where the electrophoretic layer is introduced to reduce the adsorption of entities to the surface of the chamber, second monomers of interest include: the neutral group comprising hydrophilic monomers listed above, e.g., acrylamide, hydroxyethylmethacrylate, dimethylacrylamide, vinyl pyrrolidone, low molecular weight (less than 1000 dal) polyethylene glycol acrylates, and the like; zwitterionic groups having an overall net charge of zero, such as N-(3-sulfopropyl)-N-methacryloxyethyl-N,N-dimethyl ammonium betaine, and the like; as well as polyethylene glycol acrylates of low molecular weight, and the like.

For electrophoretic layers comprising reactive functional groups, the second monomer will comprise a moiety which is the functional group. For the immobilization of an affinity agent to the surface of the chamber, reactive functional groups that provide covalent bonding to the affinity agent are of interest. Various techniques employing a variety of different functional reactive groups for the immobilization of affinity agents to the surface of polymeric substrates are known. See, e.g., Trevan, "Immobilized Enzymes, An Introduction and Applications in Biotechnology," (J. Wiley & Sons, 1980), Taylor & Dekker, eds., Protein Immobilization, Fundamentals and Applications (1991); and Walsh & Headon, "Protein Biotechnology" (J. Wiley & Sons 1994), the pertinent disclosures of which are herein incorporated by reference. Reactive functional groups of interest which can either react directly with an affinity agent or be treated to provide for groups capable of directly reacting with affinity agents include hydroxy, amino, epoxy, carboxy, amide, isocyanate, aldehyde and the like. Specific second monomers of interest include glycidyl methacrylate, acrolein and the like.

Where the surface electrophoretic layer is to substantially fill the inner volume of the chamber to provide for an electrophoretic medium, where the medium may comprise linear or crosslinked polymeric networks, second monomers of interest include acrylamide, dimethylacrylamide, other monosubstituted and disubstituted acrylamides, and the like.

The second monomer will be present in a solution, where any of a variety of solvent systems may be employed, including co-solvent systems. Solvent systems of interest include pure water and water/lower alkanol mixtures, where the lower alkanol will typically be a C4 or lower alkanol, such as ethanol, propanol, isopropyl alcohol and the like. Instead of, or in addition to, a lower alkanol, other polar organic solvents may be employed as co-solvents, such as dimethylformamide, dimethylsulfoxide and the like. The volume percent of the water in the solvent system will range from 10 to 100%. The volume percent of the co-solvent in the system, when present, will not exceed 90%, and will usually not exceed 50%. Non-aqueous solvent systems may also be employed, where the non-aqueous solvents may be selected from any convenient organic solvent, such as those listed above. The volume percent of second monomer in the solvent will generally range from about 3 to 20%, usually from about 3 to 12% and more usually from about 3 to 8%.

In addition, the second monomer solution may further comprise various agents necessary and/or desirable for the polymerization, where such agents include those agents useful in physical and chemical initiation. Chemical initiators include: persulphate+3-dimethylaminopropionitrile (DMPAN), persulphate+tetramethylethylenediamine (TEMED), persulphate, persulphate+thiosulfate, persulphate+bisulfite, persulphate+diethylmethylaminediamine (DEMED), $H_2O_2+Fe^{2+}$, benzoyl peroxide, lauroyl peroxide, tetralin peroxide, actyl peroxide, caproyl peroxide, t-butyl hydroperoxide, t-butyl perbenzoate, t-butyl diperphthalate, cumene hydroperoxide, 2-butanone peroxide, azoinitiators, e.g., azodiisobutyronitrile and azodicarbonamide, riboflavin, methylene blue+a redox couple, and the like. Preferably a chemical polymerization initiator such as persulphate will be employed.

For the preparation of cross-linked electrophoretic layers, the second monomer composition may further comprise various cross linking agents, which will be selected depending on the nature of the second monomer. For example, with acrylic monomers, e.g., acrylarnide, cross linking agents of interest include: N,N'-ethylene bisacrylamide (Bis); ethylene diacylate (EDIA); N,N'-diallyltartardiamide (DATD); N,N'-bis acrylyl cystamine (BAC); N,N'-(1,2-dihydroxyethylene)bisacrylamide (DHEBA); and the like. Other agents of interest that may be present for a variety of reasons in the composition, e.g., to provide for suitable electrophoretic sieving through the layer polymerized from the composition, include various salts, particularly buffering salts, where the concentration of the buffering salts will vary from 0.01 to 0.5 M, more usually from 0.01 to 0.1 M. The salts may include Tris, phosphate, EDTA, MOPS, and the like. Denaturing agents may also be present in the aqueous phase, including urea, SDS, formamide, methylmercuric hydroxide, alkali, and the like, where the concentration will vary depending on the particular denaturing agent, e.g., for urea, the concentration will range from about 0.1 to 9.0 M.

Following contact of the second monomer composition with the interpenetrated surface, the first and second monomers will be copolymerized. Depending on the particular second monomer composition, polymerization may already have been initiated upon preparation of the second monomer composition, e.g., where a chemical initiator such as persulphate is employed. Where polymerization is not initiated upon preparation of the second monomer composition, polymerization may then be initiated once contact is made using any convenient means, including heat, electron beam, photopolymerization, gamma radiation, microwave radiation, and the like. However, the particular polymerization technique employed will be chosen so that little or no grafting of the base polymeric material occurs during copolymerization of the first and second monomers.

Upon initiation of the polymerization in the second monomer composition, as the polymer chain extends through the second monomer composition, those second monomers near the interpenetrated surface react with the first monomers embedded in the material near the surface, which then react with first monomers further below the surface, whereby the growing polymer chain continues to extend below the surface through the interdiffused region of the polymer, adding embedded first monomers to the growing chain.

Contact of the second monomer with the surface may be either static or dynamic, depending on the desired properties of the electrophoretic layer. For example, static conditions will be employed to obtain a thick electrophoretic layer, such as those electrophoretic layers that are to serve as a gel medium. Alternatively, dynamic conditions can be employed to achieve a thinner electrophoretic layer having a more uniform surface comprising lower molecular weight networks, which may be desirable for those applications where the electrophoretic layer is to alter the inherent surface charge of the material or to provide for the introduction of certain functional groups on the surface of the material in the region of modification. Where dynamic conditions are employed for contact, the flow rate of the second monomer composition through the chamber will typically range from 10 μl/min to 5 ml/min, usually from about 25 μl/min to 3 ml/min, and more usually from about 50 μl/min to 3 ml/min.

Polymerization will be allowed to continue for sufficient time for an electrophoretic layer of desired properties to be produced, and will generally be allowed to proceed to completion. Although the exact time will vary depending on the particular nature of the system employed, usually polymerization will proceed from about 0.25 to 4 hr, usually from about 0.5 to 2 hr, and more usually from about 0.5 to 1 hr.

Following polymerization, the surface modified chamber may be further treated as necessary, depending on the electrophoretic application in which it is to be employed. For example, where the electrophoretic surface is a gel medium, the fluid phase of the gel medium may be replaced with a running buffer. Alternatively, where the electrophoretic layer comprises functional groups for covalent attachment of affinity agents such as ligand or receptors, the modified surface may be contacted with such affinity agents, and then washed to remove any unbound agents.

In other embodiments of the invention, an electrophoretic polymeric layer is coated on the surface of the base material without the aid of an anchoring polymeric layer. In these embodiments, the polymer comprising the polymeric coating layer is first dissolved in a suitable solvent, and then contacted with the surface of the base material. During this contacting step, dissolved polymer is selectively adsorbed or absorbed at the surface of the base material, and forms a surface coating. The composition of the polymer comprising the coating layer may be selected such that it has a solubility parameter similar to that of the base material, and such that it interpenetrates the surface of the base material. Such interpenetration will be promoted if the solvent carrying the polymer also has a solubility parameter similar to that of the base material, and promotes the swelling of the base material. Because the molecular weight of the polymer will be much larger than that of the monomers used in forming anchoring layers in the embodiment described earlier in this application, the interpenetration of the surface layer will not be as significant as in this earlier embodiment. However, sufficient interpenetration can be achieved to provide a stable electrophoretic polymeric layer.

Alternatively, the composition of the polymer comprising the coating layer may be selected such that it does not interpenetrate the surface of the base material, but instead forms molecular interactions with the surface of the base material. These interactions may be ionic, hydrogen bonding, or dispersive. Because each polymer molecule in the coating layer can interact with the surface at multiple locations, the additive effect of even weak interactions between repeating units on the polymer and moieties at the surface of the base material will often be sufficient to hold the electrophoretic polymer layer at the surface. In some cases, the electrophoretic polymeric layer formed in this manner may slowly dissolve into solution during electrophoretic analysis. However, the surface properties will remain relatively stable over several analyses before such slow dissolution alters these properties significantly.

Cationic and anionic polymers are suitable for deposition onto the inner walls of plastic microchannels to control electroendoosmotic effects. Examples of anionic ionomers and polyelectrolytes suitable for this type of treatment are: Nafion® (perfluorinated ionomeric membrane with perfluorinated propylene grafted chains with an ending sulfonic group), polystyrenesulfonic acid and corresponding salts, poly(vinylsulfonic acid) and its salts, poly(styrenesulfonic acid-co-maleic acid), poly(acrylic acid), poly(methacrylic acid), poly(acrylic-co-methylmethacrylate), poly(acrylamide-co-acrylic acid), poly(2-acrylamido-2-methyl-1-propanesulfonic acid) and poly(ethylene-co-acrylic acid). The presence of sulfonic groups is preferred to carboxylic groups for EOF effects independent of pH. A balance of carboxylic and sulfonic groups may be desirable to control flow with pH variations. Cationic polymers suitable for the build up of positive charges on the microchannels surface are poly(diallyldimethylammonium chloride), poly(acrylamide-co-diallyldimethylammonium chloride), and polymer with amino groups in the backbone or as part of the side groups.

The subject electrophoretic chambers find use in a variety of electrophoretic applications, where by electrophoretic applications is meant that charged entities are moved through a medium housed in a chamber under the influence of an applied electric field, where movement of the entities may be the result of either an inherent electrical charge of the entities or bulk fluid flow through the chamber. Illustrative applications are reviewed in Andrews, Electrophoresis (1990); Barron & Blanch, Separation & Purification Methods (1995) 24:1–118 and U.S. Pat. No. 5,126,022, the disclosures of which are hereby incorporated herein by reference. Illustrative applications include methods based on sample component separation and identification, e.g., sequencing, sample component purification, synthesis applications, sample preparation and the like.

The following examples are offered by way of illustration and not by way of limitation.

EXAMPLES

Example 1
Preparation of Cross-linked Polyacrylamide Gel Bound Between Two Polymethacrylate Plates and Its Use in the Electrophoretic Separation of a ΦX174/HaeIII DNA Ladder Flat polymethylmethacrylate (PMMA) plates 160×180 mm were cut from an Acrylite OP4 acrylic sheet (Cyro Industries). The plates were stringently wiped with methanol to ensure that no particles or residues were left on the surface of the plates. 10 ml of 10% dimethylacrylamide (DMA) in methanol were pipetted onto the surface of each plate. The DMA solution was gently spread using a lab paper tissue to cover the entire surface of the plates. The DMA solution was allowed to penetrate the surface of the plates for 20 minutes. After 20 minutes, the DMA solution was wiped clean using a lab paper tissue and lightly flushed with nitrogen gas. The surface was then wiped with a lab paper tissue wetted with methanol, resulting in a clear and spotless surface.

21.5 g of T5C3 (1 g of acrylamide, 35 μg of bisacrylamide and 20.5 g water) was combined with 1.0 g of 10×TBE (0.89 M tris(hydroxymethyl)aminomethane, 0.89 M boric acid and 0.05 M ethylenediaminetetraacetic acid) and 2.2 μl of 25 mM ethidium bromide solution. 150 μl of 10% ammonium persulfate solution and 75 μl N,N,N,N-tetramethylenediamine (TEMED) were added to the above solution and mixed gently. The resultant solution was poured between the two treated PMMA surfaces separated by 75 μm spacers and allowed to polymerize for about two hours. A well forming comb was introduced between the plates to form sample wells for electrophoresis.

The resultant cross-linked polyacrylamide gels had good adhesion to the PMMA plates as a result of the surface treatment. In contrast, cross-linked gels poured between two PMMA plates having untreated surfaces slid out of the plates upon removal from the casting stand.

Electrophoresis of ΦX174/HaeIII DNA fragments was performed using standard procedures with a run voltage of 7.4 V/cm for 2.25 hours. The results were visualized on a standard UV imaging system.

The non-denaturant separation of ΦX174/HaeIII DNA fragments under these conditions resolved 8 bands of the 11 possible fragments resolvable under more ideal conditions. The experiment was designed to demonstrate the resolving capacity of the gel while being attached to the surface of the PMMA plates using the described method.

The results demonstrate that the surface interpenetration method according to the subject invention can be used to stably secure an electrophoretic gel medium to the surface of a polymethylmethacrylate plate and that such a secured gel can be used successfully in electrophoretic separation.

Example 2
Preparation of Polymethylmethacrylate Capillaries Having an Inner Linear Polyacrylamide Coating The inner surface of a cleaned microbore polymethylmethacrylate (PMMA) capillary is contacted with a 10% solution of dimethylacrylamide (DMA) in methanol for 20 minutes under static conditions. After 20 minutes, the excess DMA solution is rinsed from the internal capillary surface and a fresh solution of 3% acrylamide in water with ammonium persulfate and N,N,N,N-tetramethylenediamine (TEMED) is introduced into the internal volume of the capillary. The 3% acrylamide solution is maintained in the capillary for two hours at room temperature under static conditions, allowing for copolymerization of the linear acrylamide with DMA monomers that penetrated the surface of the capillary wall. Since the copolymerization is carried out under static conditions, the linear polyacrylamide strands grow into a thick intertwining network that essentially fills the entire volume of the capillary. The resultant linear acrylamide filled polymethylmethacrylate capillary can be used in electrophoretic separation applications.

The above procedure is also carried out with the variation that the acrylamide solution is introduced into the capillary under dynamic conditions, with a flow rate of 3 ml/min. Introducing the acrylamide solution under dynamic conditions results in formation of a thin linear acrylamide layer covering the surface of the capillary.

Example 3
Preparation of Polymethylmethacrylate Capillaries Having an Inner Surface Comprising Epoxy Functional Groups.

A PMMA capillary having a DMA interpenetrated surface is contacted with a solution of glycidyl methacrylate comprising t-butyl peroxypyvalate (TBPP) under dynamic conditions, e.g., the glycidyl methacrylate is flowed through the chamber at a rate of 50 μl/min at 40° C. Copolymerization results in the presence of a thin, uniform surface polymeric layer comprising epoxy groups. The epoxy groups can then be converted to other functional groups, as may be appropriate depending on the use of the functional group, e.g., to hydroxy groups through acid hydrolysis.

Example 4
Preparation of Polymethylmethacrylate Capillaries Comprising Ion Containing Cross-linked Gels A. Capillaries Filled with Amine Containing Gel Structures A polymethylmethacrylate capillary is filled with a 20% solution of methylmethacrylate in methanol under static conditions for 30 min. The capillary is then rinsed and a fresh 15% solution of dimethylaminoethylacrylate in methanol containing 5% ethylene glycol diacrylate and 1% t-butyl peroxypyvalate (TBBP) is introduced into the capillary. Polymerization is allowed to proceed for 2 hr at 40° C. The resultant capillary is substantially filled with an amino containing gel structure which finds use in anion exchange applications, e.g., ion removal in high ionic strength samples.

B. Capillaries Filled with Sulfonic Acid Containing Gel Structures

An MMA surface interpenetrated PMMA capillary as prepared in Example 4.A. above is contacted with a 20% solution of 2-acrylamido-2-methylpropanesulfonic acid comprising 5% N,N'-ethylene bisacrylamide and 0.15% of persulfate/bisulfate in water containing 10% sodium hydroxide (pH adjusted to 7–8) under static conditions. Polymerization is allowed to proceed for 1 hr at 55° C. with careful control of the temperature of the bath. The resultant capillary comprises a sulfonic acid containing gel structure which finds use in cation exchange applications, e.g. ion removal in high ionic strength samples.

Example 5
Alteration of EOF by Surface Treatment of Polymethylmethacrylate Capillaries with an Uncharged Polymer, Poly (DMA), and with a Negatively Charged Polymer, Poly (AMPS).

A. Surface Treatment Protocol

1. Poly (AMPS). A PMMA capillary (inner diameter 75 μm, outer diameter 375 μm, 3 ft. total length) was flushed for 10 min with a solution of 50% (wt/wt) N,N-dimethylacrylamide (DMA) in methanol at room temperature under nitrogen gas at 100 p.s.i. Next, the capillary was flushed for 10 min with nitrogen gas at 100 p.s.i. The capillary was then flushed with a freshly prepared solution of 20% (wt/wt) 2-acrylamido-2-methyl propanesulfonic acid (AMPS) in water containing 0.5% ammonium persulfate (APS) and 0.2% sodium metabisulfite ($Na_2S_2O_5$) at 40° C. under nitrogen gas at 100 p.s.i. The pressure chamber and capillary were both immersed in a water bath which was heated to 40° C. Flow through the capillary ceased as polymerization of AMPS formed a gel. Finally, the capillary was flushed for about 1 hour with water at room temperature under nitrogen gas at 100 p.s.i.

2. Poly (DMA). A PMMA capillary as in Example 5.A.1. above was flushed for 10 min with a solution of 50% (wt/wt) N,N-dimethylacrylamide (DMA) in methanol at room temperature under nitrogen gas at 100 p.s.i. Next, the capillary was flushed for 10 min with nitrogen gas at 100 p.s.i. The capillary was then flushed with a freshly prepared solution of 20% DMA in water (wt/wt) containing 0.06% APS (v/v) and 0.13% TEMED (v/v) at room temperature under nitrogen at 100 p.s.i. The flow through the capillary ceased over the course of an hour as polymerization of DMA formed a gel. Finally the capillary was flushed with water for about 1 hour under nitrogen at 100 p.s.i.

B. EOF Measurements

Measurements of EOF were made with a Beckman P/ACE using the neutral marker mesityl oxide. Electropherograms were measured in 40 mM TAPS, 25 mM AMPD; pH 8.3 at a field of 230 V/cm (capillary Lt=26 cm, Ld=19 cm). Prior to EOF measurements, each capillary was subjected to preelectrophoresis for 60 min at 230 V/cm in TAPS/AMPD buffer. Electropherograms were 30 min in duration for the Poly(AMPS)-treated capillary and 60 min in duration for the Poly(DMA)-treated capillary. Mesityl oxide (1 $\mu$g/ml in TAPS/AMPD buffer) was injected for 4 sec under hydrostatic pressure. EOF values were calculated from the peak migration times.

Figure 1:
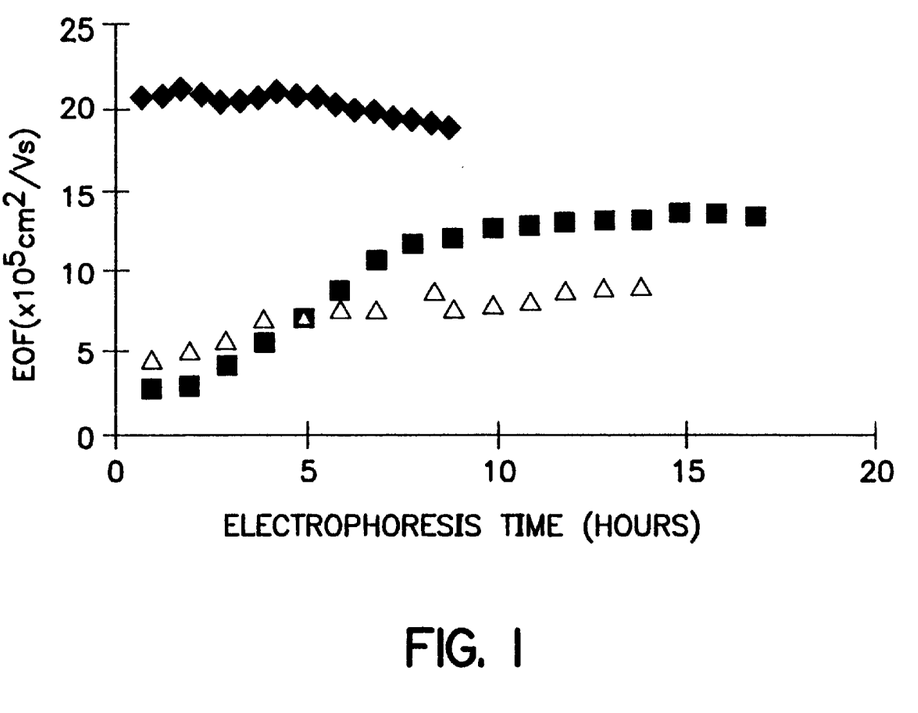
FIG. 1 is a plot of measured electroosmotic force over time, showing changes in EOF over the course of repeated electrophoresis runs in untreated PMMA capillaries (open triangles, -△-), in Poly(AMPS)-treated PMMA capillaries (filled diamonds, -◆-), and in Poly(DMA)-treated PMMA capillaries (filled squares, -■-), as described in Example 5.
Figure 2:
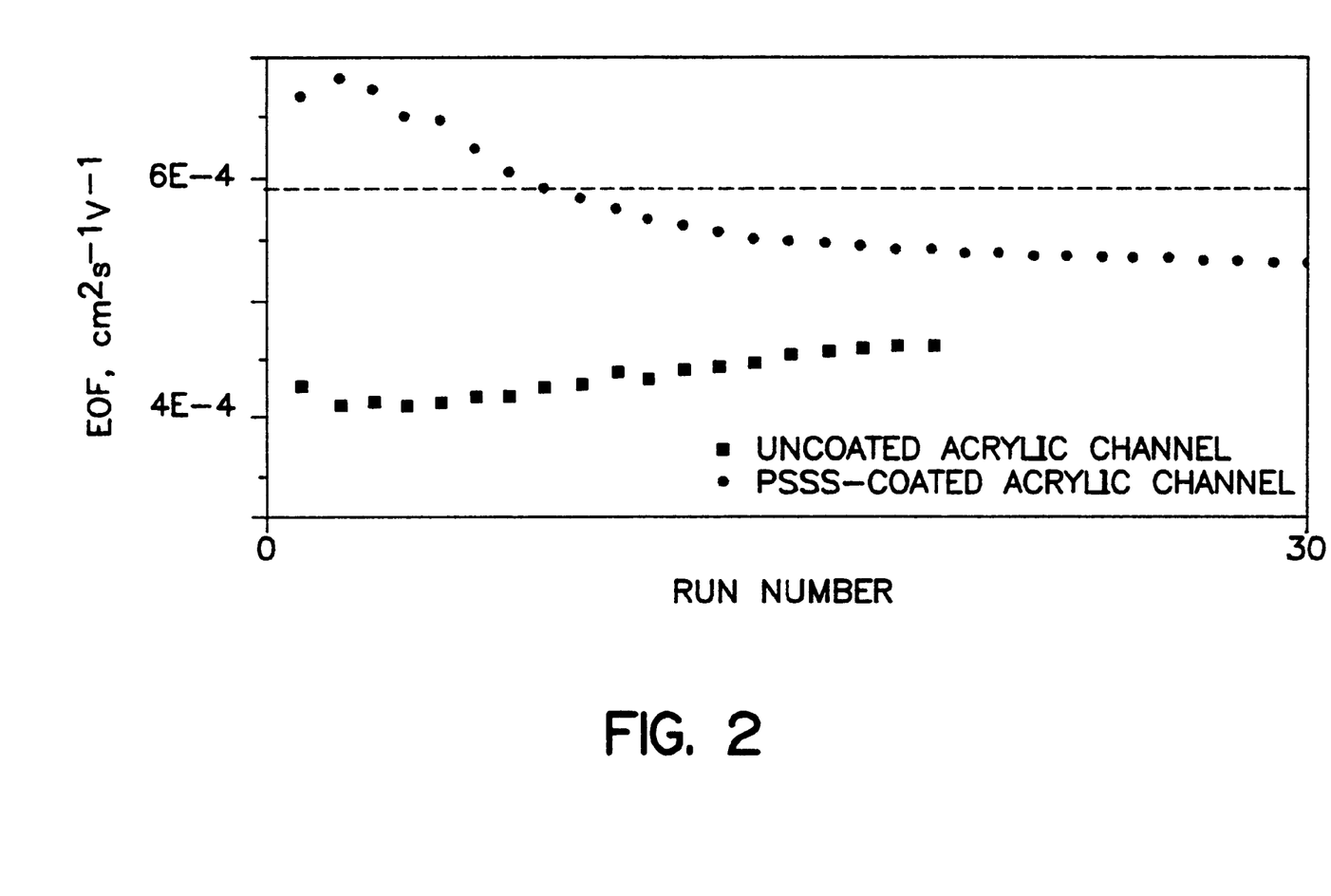
FIG. 2 is a plot of measured electroosmotic force over time, showing changes in EOF over the course of repeated electrophoresis runs in untreated PMMA channels (filled squares, -■-) and in PMMA channels treated with PSSS (filled circles, -●-), as described in Example 7.

FIG. 1 shows the results for EOF measurements in PMMA capillaries that are either untreated and that are treated by the protocols described in Example 5.A. above, which are designed to attach either of two polymeric coatings to the surface of the capillaries: an uncharged polymer, Poly(DMA); or a negatively charged polymer, Poly(AMPS). Only one series of measurements is shown for each of the treated capillaries. EOF values are plotted vs. electrophoresis time, rather than vs. trial number, to emphasize the effect of the time of successive electropherograms on the change in the measured EOF value.

As appears in FIG. 1, the capillary treated with Poly (AMPS) exhibited an initial EOF of about $20 \times 10^{-5}$ cm$^2$/Vs. The EOF decreased modestly, but steadily, during the successive 17 runs (30 min per run). After 9.5 hours of electrophoresis, the EOF had decreased by about 6%.

The capillary treated with Poly(DMA) exhibited a much greater change over the same duration of EOF measurement. Initially, the EOF was very low, but it increased dramatically (~260%) over the first 10 runs (60 min per run) before reaching a plateau at about $13 \times 10^{-5}$ cm$^2$/Vs.

The change in the measured EOF values for both treated capillaries over the course of successive electrophoretic measurements suggests that the coatings are progressively removed as a result. These initial results suggest that the Poly(DMA) coating is removed much more quickly than the Poly(AMPS) coating. In the Poly(DMA) treated capillaries, the pH 8.6 buffer employed during measurement of EOF may have caused hydrolysis of amide groups to carboxylic groups on the Poly(DMA) coating, adding negative charges at the surface and enhancing the EOF values as a result. If degradation were limited to progressive stripping away of the applied coating layer, then the EOF measurements would be expected to approach those of the untreated polymer surface.

Example 6
Alteration of EOF by Surface Deposition of Nafion® onto a Polymethylmethacrylate Electrofluidic Channel of 400 $\mu^2$ Cross-section.

Microchannel surfaces are modified as follows. Pre-treat the surface of the microchannels by flushing isopropanol for 2 minutes through the wells accessing the microchannels in the microfluidic device. Fill the microchannels with a 0.5% solution of Nafion® perfluorinated ion-exchange powder, diluted with isopropanol from a commercially available solution of Nafion® in water-alcohol mixtures (Aldrich, Catalog No 27,470-4). Nafion® is a perfluorinated ion-exchange material, see Aldrichimica Acta, 19(3):76 (1986); J. Electrochem. Soc., 140:2279 (1993). Careful filling is required to avoid bubble formation within the channels. Allow the solution to stabilize within the channel for 5–10 minutes. Using a vacuum pump pull the solution from the channels slowly. Total time for this process varies depending on the channel pattern on the microfluidic device. The process will extract the solvent from the channels leaving behind a layer of Nafion® ionomer non-covalently bound to the acrylic surface of the channel, uniformly applied over the surface of the channel. This procedure provides surface modified channels with an EOF highly independent of pH and about 30% lower than those measured with standard uncoated fused silica capillaries of equivalent cross-section. Microchannels coated using this procedure are stable for about 2 hours of analytical work.

Example 7
Alteration of EOF by Surface Deposition of Poly(sodium 4-styrenesulfonate) (PSSS) on to a polymethylmethacrylate electrofluidic channel of 400 $\mu$m$^2$ cross-section Microchannel surfaces are modified as follows. Flush the microchannels with a 3.3% solution of PSSS in water for up to 16 hours. Using a vacuum pump, pull the solution from the channels slowly. Continue the evacuation of the channels for about 30 minutes to completely dry and stabilize the layer of PSSS polymer bound to the acrylic surface. This procedure provides an EOF of the order of 5.8 10$^{-4}$ cm$^2$s$^{-1}$V$^{-1}$ measured at pH 8.6 of 50 mM TRIS buffer. The coatings are stable for about 15 runs during 2 hours of analysis.

Example 8
Alternative Process for EOF Modification by Surface Deposition of Poly(sodium 4-styrenesulfonate) (PSSS) on to a Polymethylmethacrylate Electrofluidic Channel of 400 $\mu$m$^2$ Cross-section Microchannel surfaces are modified as follows. Pre-treat the surface of the microchannels by flushing isopropanol for 2 minutes through the wells accessing the microchannels in the microfluidic device. Flush the microchannels with a 3.% solution of PSSS in water for up to 16 hours. Bubble formation should be avoided during the filling by sparging the solution with helium gas after the dissolution of the polymer in water. Using a vacuum pump, pull the solution from the channels slowly. Continue the evacuation of the channels for about 30 minutes to completely dry and stabilize the layer of PSSS polymer bound to the acrylic surface. This procedure provides an EOF of the order of 5.8 10$^{-4}$ cm$^2$s$^{-1}$V$^{-1}$ measured at pH 8.6 of 50 mM TRIS buffer. The coatings are stable for about 15 runs during 2 hours of analysis.

Example 9
Improved Process for Alteration of EOF by Surface Deposition of Nafion® onto a Polymethylmethacrylate Electrofluidic Channel of 400 $\mu$m$^2$ Cross-section Microchannel surfaces are modified as follows. Fill the microchannels with a 0.5% solution of sodium equilibrated Nafion®, diluted with isopropanol. This solution is prepared by titration with sodium hydroxide to pH 7 of a commercially available solution of Nafion® in water-alcohol mixtures (Aldrich, Cat. No. 27,470-4). Careful filling is required to avoid bubble formation within the channels. Equilibrate for 5–10 minutes. Pump out the solution from the channels slowly. Repeat the process in five more cycles of filling and evacuation of the channels with 0.5% solution of sodium equilibrated Nafion®. Bake the coated channels for 30 minutes at 104° C. This process provides surface modified channels with an EOF highly independent of pH, and more stable than that observed when surface modifying as in Example 6.

It is evident from the above results and discussion that the subject invention provides a powerful methodology for the tailoring of the surface properties of an electrophoretic chamber to best suit the needs of a particular application. With the subject invention, electrophoretic mediums stably secured to the surface of the chamber material can be fabricated. Furthermore, one can readily control the nature of the functional groups introduced on the surface, providing for a homogenous surface where desired. With the subject methodology one can also provide for a tailored surfaces having a plurality of regions of different modification, which greatly increases the number and nature of applications in which the subject chambers can be employed.

All publications and patent applications mentioned in this specification are incorporated herein by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a device comprising an electrophoretic chamber for moving entities through a medium and means for providing an applied electric field, said chamber comprising a rigid polymeric base material, the improvement which comprises:

a polymeric layer noncovalently bonded to a surface of said base material wherein said polymeric layer is different from said polymeric base material and changes the surface charge characteristics of said base material.

2. A device according to claim 1, wherein said polymeric base material is acrylic polymer.

3. A device according to claim 2, wherein said polymeric layer is an anionic polymer.

4. A device according to claim 3, wherein said anionic polymer is a perfluorinated polymer with sulfonic groups.

5. A device according to claim 2, wherein said polymeric layer is a cationic polymer.

6. A method for producing a device according to claim 1, said method comprising:

contacting a surface of said rigid polymer base material in said chamber with a polymeric solution of a polymer different from said base polymeric material and having a different charge characteristic from said base polymeric material, whereby said polymer in said polymeric solution interdiffuses into said base polymeric material and becomes bonded to said base polymeric material and forms a coating thereon.

7. A method according to claim 6, wherein said base polymeric material is acrylic.

8. In a device comprising an electrophoretic chamber for moving entities through a medium and means for providing an applied electric field, said chamber comprising a rigid polymeric methyl methacrylate base material, the improvement which comprises:

a polymeric layer noncovalently bonded to a surface of said base material, wherein said polymeric layer is a perfluorinated ionomeric membrane with perfluorinated propylene grafted chains ending in sulfonic groups.

* * * * *